United States Patent [19]

Tchernatinsky

[11] Patent Number: 4,720,357

[45] Date of Patent: Jan. 19, 1988

[54] NEW PROCESS FOR MANUFACTURING DERIVATIVES OF 17 ALPHA-HYDROXY 19-NOR PROGESTERONE AND NOVEL INTERMEDIATES FOR USE THEREIN

[75] Inventor: Claude Tchernatinsky, Beausoleil, France

[73] Assignee: Laboratoire Theramex, Monaco

[21] Appl. No.: 766,481

[22] Filed: Aug. 19, 1985

[51] Int. Cl.$^4$ .............................................. C07J 1/00
[52] U.S. Cl. .............................. 260/397.3; 260/397.4
[58] Field of Search ........................... 260/397.3, 397.4

[56] References Cited

U.S. PATENT DOCUMENTS 3,314,944  4/1967  Diassi et al. ...................... 260/397.4
3,726,864  4/1973  Phillipps et al. .................. 260/397.3
4,224,320  9/1980  Dahl et al. ........................ 260/397.4

Primary Examiner—Leonard Schenkman
Assistant Examiner—Joseph A. Lipovsky
Attorney, Agent, or Firm—Gifford, Groh, VanOphem, Sheridan, Sprinkle & Dolgorukov

[57] ABSTRACT

A process for making a known 6-methyl, 19-nor-pregna-4, 6-diene, 3.20-dione which begins with formylating a 3-alcoxy, 19-nor-pregna-3,5,17(20)-triene at the 6 position. The 6-formylated derivative is reduced to yield a 6-hydroxy methylated derivative, which is in turn dehydrated to a 3-keto, 6-methylenic derivative. The 3-keto derivative is then isomerized to a 3-keto, 4,6,17-pregnatriene. This latter triene is then coverted to the known product by reaction with a bis-hydroxylating agent and a catalyst based on osmium tetroxide. Optionally, the product can be acylated at the 17-alpha position. The process reduces the cost of producing the known product by allowing it to be manufactured from starting materials less costly than those previously required.

12 Claims, No Drawings

NEW PROCESS FOR MANUFACTURING DERIVATIVES OF 17 ALPHA-HYDROXY 19-NOR PROGESTERONE AND NOVEL INTERMEDIATES FOR USE THEREIN

This invention relates to the preparation of derivatives of 17α-hydroxy 19-nor progesterone.

The invention more precisely relates to a novel process for manufacturing derivatives of 17α-hydroxy 19-nor progesterone having the general formula I:

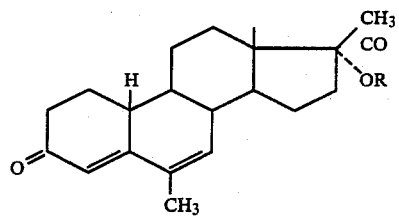

wherein R is a hydrogen or the acyl residue from an organic aliphatic carboxylic acid which is saturated or unsaturated in the hydrocarbon chain.

These compounds show a significant interest from a technical and therapeutical point of view due to the fact they are endowed with several pharmacological properties namely progestative and anti-androgenic properties. The leading compound 17 6-methyl 19-nor pregna 4, 6-dien 3,20-dione has been the subject matter of an article in Arzneimittel Forschung which fully illustrates the pharmacological properties of this group of compounds.

The compounds of general formula are already disclosed and they have been described in the literature, more particularly in the British patent 1.515.284 (to J. M. GASTAUD). In this literature the compounds of general formula I are prepared from 17α-hydroxy 19-nor pregna-4ene 3,20-dione which is also named 19-nor progesterone. This starting material is a steroidal compound belonging to the family of 19-nor pregnane.

The great interest shown by the compounds of general formula I requires that they may be prepared on an industrial scale and it appears necessary to provide a process of manufacturing the said compounds from steroidal starting material which may be available more economically and at a more extended scale.

This invention provides a new process for manufacturing the compounds of formula I which comprises the steps of reacting a 3-alcoxy 19-nor pregna 3, 5, 17 (20)-triene having the formula II:

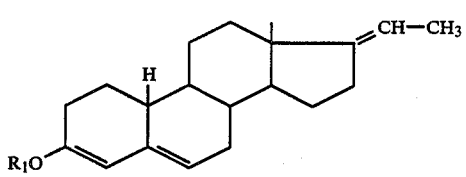

wherein $R_1$ is a lower alkyl radical or a cyclo lower alkyl radical in the form of a E or Z isomer with a formylating agent in the conditions of the Vilmeier-Hack's reaction to produce a 6-formylated derivative of the formula III:

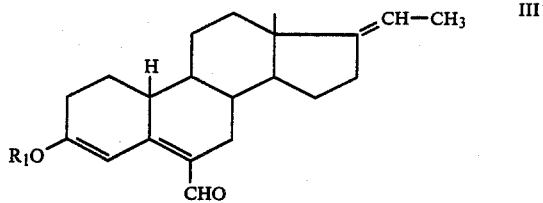

wherein $R_1$ has the same meaning as previously given reducing the latter by means of a reducing agent to produce a 6-hydroxymethylated derivative of the formula IV

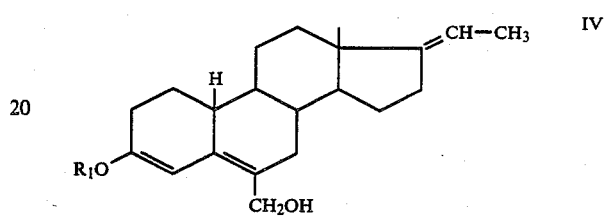

wherein $R_1$ has the same meanings as previously given contacting the compound of formula IV with an acid selected from the group consistiting of a strong mineral acid or organic acid to form the 3-keto 6-methylenic derivative of formula V:

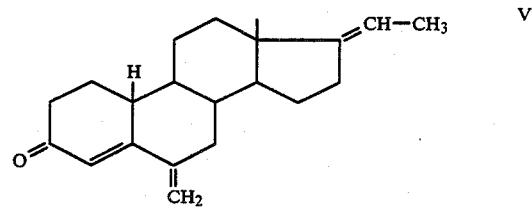

isomerizing the said compound V by means of an isomerizing catalytic agent in an inert medium to produce the 3-keto 4, 6,17-pregna triene of the formula VI:

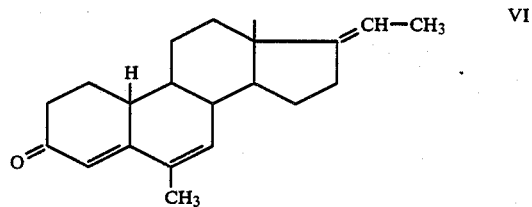

converting the latter into a compound of formula I in which R is hydrogen

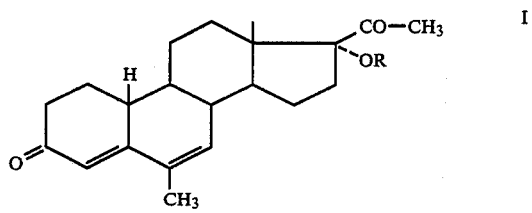

by means of a bis-hydroxylating agent in an inert solvent and in the presence of a catalyst based on osmium tetroxyde and when desired reacting the compound of formula I wherein R is hydrogen with an acylating agent to produce a compound of formula I

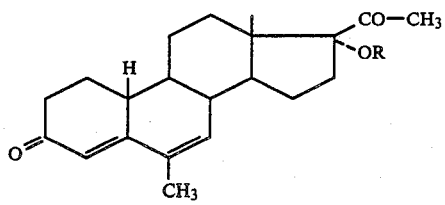

wherein R is the acyl residue of an organic aliphatic carboxylic acid having from 1 to 18 carbon atoms in the saturated hydrocarbon chain or 2 to 18 carbon atoms in a unsaturated hydrocarbon chain which may further include 1 to 5 double bonds.

The process according to this invention may also be defined by the following features which are presently the preferred ones:

1. The formylating agent is a Vilsmeier's reagent namely obtained by reacting phosgene or phosphorous oxychloride with a substituted formamide as for example dimethyl formamid. The reaction may be performed in the substituted formamide as the solvent with or without a diluting agent, the chlorimated solvents being the most preferred ones.

2. The reducing agent is preferably a mixed alkali-metal hydride and more precisely an alkali metal borohydride of the formula $BH_4M$ wherein M is an alkali metal such as sodium, potassium or lithium.

3. The dehydratation of a compound of formula IV is performed by means of a mineral acid, preferably a strong one or of an organic acid such as oxalic acid, acetic acid in an inert solvent such as a lower alkanol, for example methanol. This reaction is carried out at a temperature ranging from 0° to 50°, preferably at room temperature.

4. The isomerization of a compound of formula V is performed by means of a isomerization catalyst, namely of a metal of the platinum family on a carrier as for example palladium or charcoal. This reaction is performed in an inert solvent, such as a lower alkanol in the hot at a temperature ranging from the room temperature to 120°.

It may be convenient to add to the reaction mixture one or more compounds which show buffering properties such as sodium acetate or potassium acetate.

5. The conversion of the compound of formula VI to a 17α-hydroxy 19-nor progesterone is performed by means of a bis hydroxylating reagent such as a hydroperoxyde of an amine-oxyde. The most preferred bis hydroxylating agents are the hydroperoxyde of N-oxyde of triethylamine or the hydroperoxyde of N-oxyde of N-methylmorpholine.

The conversion is performed in an inert solvent such as a tertiary alkanol as for example tert butanol.

The conversion is also performed in the presence of catalytic amounts of osmium tetroxyde in an organic basic medium such as pyridine.

6. The acylation of the 17α-hydroxy 19-nor progesterone is performed using a functional derivative of an organic carboxylic acid such as an acid halide, preferably the acid chloride: an organic carboxylic anhydride or a mixed organic carboxylic anhydride such this formed by reacting a carboxylic acid with a dialkyl- or dicycloalkyl carbodiimide.

As far as the invention is concerned the isomers E and Z relate to the conformation of the 17-20 ethylidenic chain. The invention encompasses the pure E or Z isomers as well as the mixtures of the same in any proportion.

Further this invention includes the intermediate compounds of formula III, IV and V as a part of the invention.

The words lowers alkyl are intended to designate a hydrocarbon chain having from 1 to 6 carbon atoms such as methyl, ethyl, isopropyl or neopentyl.

The words "lower cycloalkyl" are intended to designate a saturated cyclic structure having from 3 to 7 carbon atoms such as cyclopropyl, cyclobutyl, cyclopentyl or cyclohexyl.

The examples are merely illustrative of the invention. They do not limit it in any manner.

PREPARATION OF THE STARTING MATERIAL OF FORMULA II (A) 3-methoxy 19-nor pregna 3, 5, 17 (20)-triene (isomer E or trans)

(a) From 17α-ethynyl-estradiol 3-methyl ether

Using the same method as described by F. B. Colton (J. of Am. Chem. Soc. 79 (1957) 1123, 19-nor pregna 4, 17 (20)-diene 3-one is obtained which by reaction with methyl orthoformate in acidic medium gives rise to 3-methoxy 19-nor pregna 3, 5, 17 (20)-triene (isomer trans) MP=90°, $[\alpha]_D = -365°$, λ max 242 mu, ε=1900.

(b) From 3-methoxy 19-nor pregna 2, 5, (10) 17 (20)-triene (isomer trans)

21 g 3-methoxy 19-nor pregna 2, 5 (10) 17 (20)-triene (isomer trans) are dissolved in 420 ml chloroform. To this solution 0,21 g tris (triphenyl-phosphine) Rhodium chloride is added and the whole mixture is heated to reflux for one hour. The solution is distilled off under reduced pressure and the dry residue is let to cristallize after having taken it up in methanol—17 g 3-methoxy 19-nor pregna 3, 5, 17 (20)-triene (isomer trans) are thus recovered i.e. a yield of 81%. The pure compound melts at 94° C.

(c) From 3, 17-dioxo estra 4-ene 1-3-methoxy 17-oxo estra 3,5-diene 10 g 3, 17-dioxo estra 4-ene in 50 ml methanol are mixed under stirring with 10 ml methyl orthoformate and 50 mg p. toluene sulphonic acid. Few drops of triethylamine are added thereto then the mixture is chilled and the crystalls are separated then dried—3-methoxy 17-oxo estra 3, 5-diene are thus obtained with a yield of 69%.

2. A mixture of 9 g diethyl 2-cyclohexylimino ethyl phosphonate and 1 g sodium hydride (oily paste at 80%) is prepared in 90 ml tetrahydrofuran at 0° for one hour under a stream of nitrogen. To this suspension 7 g 3-methoxy 17-oxo estra 3, 5-diene are added and the mixture is kept under stirring for 24 hours at room temperature. A solution of 30 ml water, 7 ml acetic acid, and 14 g potassium acetate is carefully added and the whole is stirred for 2 hours, then a saturated aqueous solution of sodium chloride. The organic phases are separated and washed as usually with a saturated solution of sodium chloride. The solvent is distilled off and raw 3-methoxy 21-oxo 19-nor pregna 3, 5, 17 (20) triene is recovered.

The compound is dissolved in 45 ml tetrahydrofuran and reacted for 1 hour at the reflux temperature with an ethereous solution of 2 g lithium aluminohydride and 4 g aluminium chloride.

The mixture is cooled, treated with an aqueous solution of ammonium chloride and after having extracted it, 5.5 g 3-methoxy 19-nor pregna 3, 5, 17 (20)-triene (isomer trans) are recovered.

(B) 3-ethoxy 19-nor pregna 3, 5, 17 (20)-triene (isomer trans)

5 g 3-oxo 19-nor pregna 4, 17 (20)-diene (isomer trans) are dissolved in 50 ml ethanol to which 5 ml ethyl orthoformate and 25 mg p. toluenesulphonic acid are added. The mixture is stirred for 15 mn at room temperature then neutralized by adding a few drops of triethylamine.

The solvent is distilled until reduced volume then the mixture is cooled and let to crystallize in a cool place. The crystalls are separated by filtration then dried—3-ethoxy 19-nor pregna 3, 5, 17 (20)-triene (isomer trans) is thus obtained with a yield of 78%.

(C) 3-methoxy 19-nor pregna 3, 5, 17 (20)-triene (isomer cis E or Z)

(a) From 3-methoxy 17-oxo estra 1, 3, 5 (10)-triene

This compound is converted into 3-methoxy 19-nor pregna 1, 3, 5 (10), 17 (20) tetraene (isomer cis) according to the technique described by Krubiner and Oliveto (J. of Org. Chem. 31 (1966) 24. The latter is hydrogenated according to the Birch-Nelson's method to provide after recrystallization from ethanol 79% of 3-methoxy 19-nor pregna 2, 5 (10) 17 (20)-triene (isomer cis) which melts at 113°.

By action of dilute hydrochloric acid, the 3-methyl ether is converted into 3-oxo 19-nor pregna 4, 17 (20)-diene (isomer cis- which is further reacted with methyl orthoformate and p. toluene sulphonic acid to produce 3-methoxy 19-nor pregna 3, 5, 17 (20)-triene (isomer cis). MP=94°.

(b) From 3-methoxy 19-nor pregna 3, 5 (10) 17 (20)-triene (isomer cis)

The isomerization step thereof is performed according to the procedure described in preparation A b).

(c) From 3, 17-dioxo estra 4-ene 9.6 g 3-methoxy 17-oxoestra 3, 5-diene are dissolved in 30 ml dimethylsulphoxyde and to this 7 g (triphenylethyl) phosphonium bromide then 2 g potassium tertbutylate are added. The mixture is heated for 16 hours at 60° then let to revert to room temperature and extracted with hexane. The hexanic phases are separated, distilled off and the dry residue is taken up in methanol from which the pregnatriene crystallizes 3-methoxy 19-nor pregna 3, 5, 17 (20) triene (isomere cis) is obtained with a yield of 84%.

(d) 3-ethoxy 19-nor pregna 3, 5, 17 (20)-triene (isomer cis)

This compound is obtained starting from 3-oxo 19-nor pregna 4, 17 (20)-diene according to the procedure described in paragraph B. MP=125°, [α]D=−181°, λ max 242 mu, ε=19160

EXAMPLE I 3,20-dioxo 6-methyl 17α-hydroxy 19-nor pregna 4,6-diene

Step A: 3-methoxy 6-formyl 19-nor pregna 3, 5, 17 (20)-triene (isomer trans)

To a solution of 16.4 g 3-methoxy 19-nor pregna 3, 5, 17 (20)-triene (isomer trans) in 135 ml dimethylformamide, a Vilsmeier's reagent made from 72 ml dimethylformamide and 9 ml phosphorous oxychloride is added at 0°. After 30 mn contact, a solution of 33 g sodium acetate in 80 ml water is slowly added. The aqueous solution is extracted three times with methylene chloride which is separated and washed with an aqueous solution of sodium bicarbonate.

After the usual treatments, the dry residue is recrystallized from methanol to recover pure 3-methoxy 6-formyl 19-nor pregna 3, 5, 17 (20)-triene (isomer trans) with a yield of 84%. MP=110°, λ max 323 mμ, ε=12900

Using the same procedure starting from 3-methoxy 19-nor pregna 3, 5, 17 (20)-triene (isomer cis), 3-methoxy 6-formyl 19-nor pregna 3, 5, 17 (20)-triene (isomer cis) is obtained. MP=110°, [α]D=−240°, λ max 324 mμ, ε=14400.

Step B: 3-methoxy 6-(hydroxymethyl) 19-nor pregna 3, 5, 17 (20)-triene (isomer trans)

12 g 3-methoxy 6-formyl 19-nor pregna 3, 5, 17 (20) triene (isomer trans) are dissolved in 120 ml methanol to which 720 mg sodium borohydride are added.

The mixture is kept under stirring for 45 mn at 5°, then 80 ml water is added. The crystalls of 3-methoxy 6-(hydroxymethyl) 19-nor pregna 3, 5, 17 (20)-triene (isomer trans) are dried. The yield amounts to 95%.

Similarly 3-methoxy 6-(hydroxymethyl) 19-nor pregna 3, 5, 17 (20)-triene (isomer cis) is obtained from 3-methyl 6-formyl 19-nor pregna 3, 5, 17 (20)-triene (isomer cis).

Step C: 3-oxo 6-methylene 19-nor pregna 4, 17 (20)-diene (isomer trans)

10 g 3-methoxy 6-(hydroxymethyl) 19-nor pregna 3, 5, 17 (20)-triene (isomer trans) are dissolved in 90 ml methanol to which 10 ml 2N hydrochloric acid are added and stirred for 5 mn. The crystals are dried, washed and throughly dried 3-oxo 6-methylene 19-nor pregna 4, 17 (20)-diene (isomer trans) is obtained with a yield of 97%. MP=105°, [α]D=−203°, λ max 261 mμ, ε=10500

Similarly starting from 3-methoxy 6-(hydroxymethyl) 19-nor pregna 3, 5, 17 (20)-triene (isomer cis) 3-oxo 6-methylene 19-nor pregna 4, 17 (20)-diene (isomer cis) is obtained. MP=148°, [α]D=+206°, λ max=266 mμ, ε=11500

Step D: 3-oxo 6-methyl 19-nor pregna 4, 6, 17 (20)-triene (isomer trans)

A mixture of 2 g 3-oxo 6-methylene 19-nor pregna 4, 17 (20)-diene (isomer trans), 2 g sodium acetate 800 mg of palladium on Charcoal at 5% Pd and 200 ml ethanol at 95% is heated to reflux for 1 hour, then filtered and distilled off.

The dry residue is taken up in chloroform, the solution is filtered, washed with water and evaporated to dryness. The thus obtained only residue is distilled. The resulting oil substantially consists of 3-oxo 6-methyl 19-nor pregna 4, 6, 17 (20)-triene (isomer trans). [α]D=−53°, λ max=290 mμ, ε=22100

Similarly 3-oxo 6-methyl 19-nor pregna 4, 6, 17 (20)-triene (isomer cis) is obtained from 3-oxo 6-methylene 19-nor pregna 4, 17 (20)-diene (isomer cis). The same is an oily liquid [α]D=+92°.

EXAMPLE II 3, 20-dioxo 6-methyl 17-hydroxy 19-nor pregna 4,6-diene 10 g 3-oxo 6-methyl 19-nor pregna 4, 6, 17 (20)-triene (isomer cis), 100 ml tert-butanol and 50 mg osmium tetroxyde are mixed together—14 g of the complex hydroperoxyde of N-triethylamine oxyde is added thereto. The mixture is let to stirr for 24 hours at room temperature. To this 10 g celite and 6 g sodium sulphite previously dissolved in 200 ml water are threrafter added. The aqueous phase is extracted with toluene. The toluenic phase is separated and filtered on a layer of silica (chromatographic grade). The eluate is evaporated off and the residue is cristallized from methanol—3.20-dioxo 6-methyl 17α-hydroxy 19-nor pregna 4,6-diene is obtained with a yield of 63% MP=206°, λ max=201 mμ=2400.

The same compound is also obtained using the same procedure starting from 3-oxo 6-methyl 19 nor-pregna 4, 6, 17 (20)-triene (isomer trans).

EXAMPLE III 3, 20-dioxo 6-methyl 17-acetoxy 19-nor pregna 4,6-diene 10 g of 3.20-dioxo 6-methyl 17α-hydroxy 19-nor pregna 4,6-diene are dissolved in 50 ml chloroform.

A mixture of 7 ml acetic anhydride and 1 g p. toluene sulphonic acid is added thereto. The whole mixture is heated under a stream of nitrogen to the reflux, then let to revert to about 40° C.

A mixture of 10 ml methanol and 1 ml concentrated hydrochloric acid is added thereto. The reaction mixture is anew heated to reflux for 1 hour then cooled to room temperature, washed with dilute sodium hydroxyde then with water until neutral. The organic phase is distilled off. The residue is taken up in methanol from which crystals of 3,20-dioxo 6-methyl 17-acetoxy 19-nor pregna 4,6-diene separate. The yield amounts to 80%.

What we claim is:

1. A process for manufacturing 6-methyl, 19-nor-pregna-4, 6-diene, 3,20-diones of the formula (I):

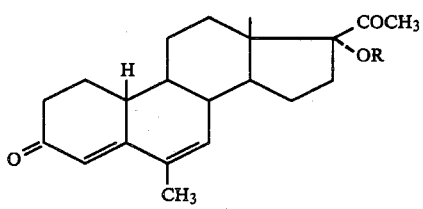

wherein R is hydrogen or the acyl residue of a saturated or unsaturated organic carboxylic acid having from 1 to 18 carbon atoms in a saturated hydrocarbon chain or from 2 to 18 carbon atoms in an unsaturated hydrocarbon chain which may include from 1 to 5 double bonds in a straight or branched chain, which comprises the steps of:

reacting a 3-alcoxy, 19-nor-pregna-3, 5, 17 (20)-triene of the formula (II):

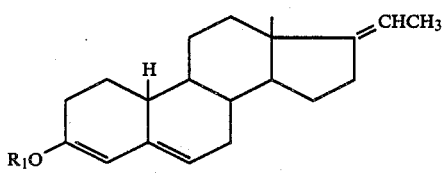

wherein $R_1$ is a lower alkyl radical or a cyclo-lower alkyl radical, in the form of an E or Z isomer, with a formylating agent under the conditions of Vilsmeier's reaction to produce a 6-formylated derivative of the formula (III):

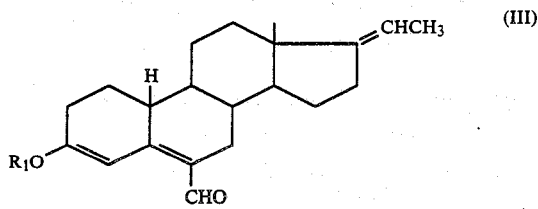

wherein $R_1$ has the same meaning as previously given;
reducing said 6-formylated derivative by means of a reducing agent to produce a 6-hydroxymethylated derivative of the formula (IV):

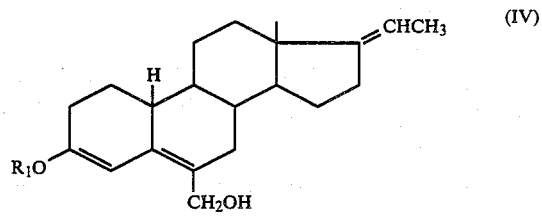

in the form of an E or Z isomer, wherein $R_1$ has the same meaning as previously given;
contacting said 6-hydroxymethylated derivative with a dehydrating mineral or organic acid to form a 3-keto, 6-methylenic derivative of the formula (V):

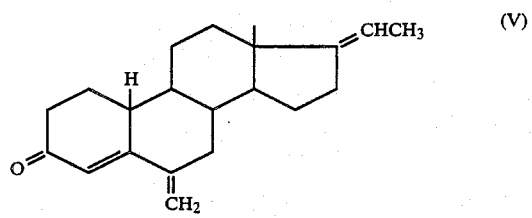

in the form of an E or Z isomer;
isomerizing said 3-keto, 6-methylenic derivative by means of an isomerizing catalytic agent in an inert medium to produce a 3-keto, 4, 6, 17-pregna-triene of the formula (VI):

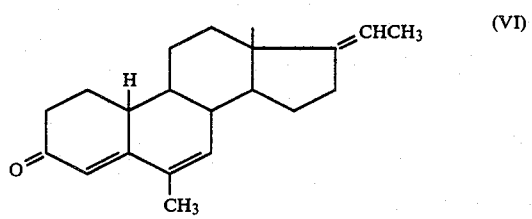

in the form of an E or Z isomer; and
converting said 3-keto, 4, 6, 17-pregna-triene into 6-methyl, 17-alpha-hydroxy, 19-nor-pregna-4, 6-diene, 3,20-dione, that is, the specific compound of formula (I) wherein R is hydrogen, by means of a bis-hydroxylating agent in an inert solvent and in the presence of a catalyst based on osmium tetroxide; and optionally reacting said 17-alphahydroxy, 6-methyl, 19-nor-pregna-4, 6-diene, 3,20-dione with an acylating agent to produce the remaining compounds of formula (I) wherein R is other than hydrogen.

2. A process according to claim 1, wherein said formylating agent is a Vilsmeier's reagent made from phosgene or phosphorous oxychloride and a substituted formamide.

3. A process according to claim 1, wherein said reducing agent is a mixed alkali metal hydride.

4. A process according to claim 1, wherein said dehydratation of said 6-hydroxymethylated derivative of formula (IV) is performed by means of a strong mineral acid or an organic acid in an inert solvent.

5. A process according to claim 1, wherein said isomerization of said 3-keto, 6-methylenic derivative of formula (V) is performed by means of an isomerization catalyst based on a metal of the platinum family.

6. A process according to claim 1, in which said conversion of said 3-keto, 4, 6, 17-pregna-triene of formula (VI) into said 17-alpha-hydroxy, 19-nor progesterone is performed by means of a bis-hydroxylating reagent based on a hydroperoxide of a N-amine oxide.

7. A process according to claim 1, in which said conversion of said 3-keto, 4, 6, 17-pregna-triene of formula (VI) is performed in the presence of a catalytic amount of osmium tetroxide.

8. A process according to claim 1, wherein said acylation of said 17-alpha-hydroxy, 19-nor progesterone is performed using an acylating functional derivative of an organic carboxylic acid.

9. As intermediate compounds in the process of claim 1, the compounds of formula (III):

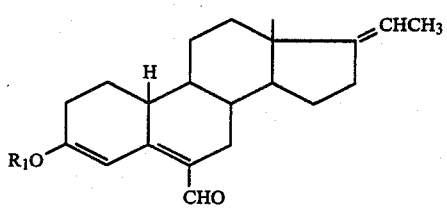

wherein $R_1$ has the same meaning as previously given.

10. As intermediate compounds in the process of claim 1, the compounds of formula (IV):

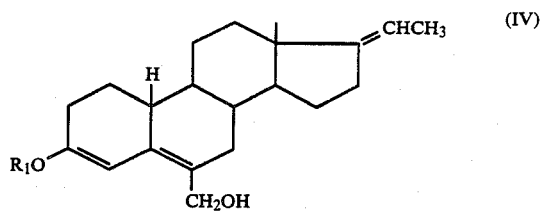

wherein $R_1$ has the same meaning as previously given, in the form of an E or Z isomer.

11. As an intermediate compound in the process of claim 1, the compound of formula (V):

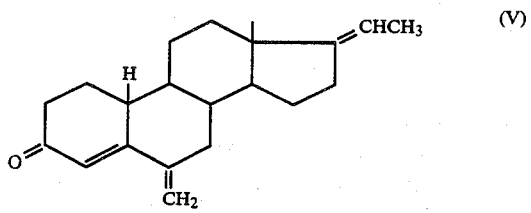

in the form of an E or Z isomer.

12. As an intermediate compound in the process of claim 1, the compound of formula (VI):

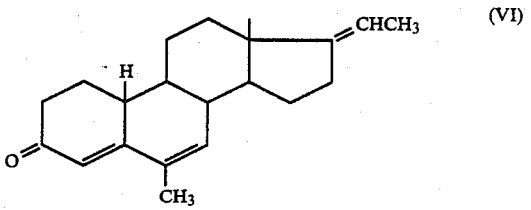

in the form of an E or Z isomer.

* * * * *